United States Patent
Foresta et al.

(12) 
(10) Patent No.: US 6,242,497 B1
(45) Date of Patent: Jun. 5, 2001

(54) USE OF 6,7-SUBSTITUTED 2-AMINOTETRALINES SUITABLE FOR PREPARING A PHARMACEUTICAL COMPOSITION FOR THE THERAPEUTIC TREATMENT OF INFLAMMATORY AND/OR AUTOIMMUNE PATHOLOGIES

(75) Inventors: Piero Foresta; Vito Ruggiero, both of Rome (IT)

(73) Assignee: Sigma-Tau Industrie Farmaceutiche Riunite S.p. A., Rome (IT)

( * ) Notice: Subject to any disclaimer, the term of this patent is extended or adjusted under 35 U.S.C. 154(b) by 0 days.

(21) Appl. No.: 09/533,066

(22) Filed: Mar. 22, 2000

(30) Foreign Application Priority Data

Sep. 22, 1997 (IT) ........................................ 000569

(51) Int. Cl.$^7$ ................................................. A61K 31/135
(52) U.S. Cl. ................................................. 514/657
(58) Field of Search ............................................. 514/657

(56) References Cited

U.S. PATENT DOCUMENTS

| 5,591,777 | * | 1/1997 | Foresta et al. | 514/563 |
| 5,637,614 | * | 6/1997 | Foresta et al. | 514/548 |
| 5,962,525 | * | 10/1999 | Foresta et al. | 514/548 |

* cited by examiner

Primary Examiner—Raymond Henley, III
(74) Attorney, Agent, or Firm—Nixon & Vanderhye

(57) ABSTRACT

6,7-substituted 2-aminotetralines are used to treat inflammatory and/or autoimmune conditions induced by inflammatory cytokines.

12 Claims, No Drawings

USE OF 6,7-SUBSTITUTED 2-AMINOTETRALINES SUITABLE FOR PREPARING A PHARMACEUTICAL COMPOSITION FOR THE THERAPEUTIC TREATMENT OF INFLAMMATORY AND/OR AUTOIMMUNE PATHOLOGIES

The present invention relates to the use of 6,7-substituted-2-aminotetralines and their pharmacologically acceptable salts suitable for the prophylactic and therapeutic treatment of septic shock and for the treatment of inflammatory and/or autoimmune pathologies which will be better defined here below, in which the aetiopathogenetic role of inflammatory cytokines is well established.

6,7-Substituted-2-aminotetralines, which are active in the treatment of septic shock, are well known. EP-A-073086 1, which is incorporated herein for reference purposes, describes a class of such 6,7-substituted-2-aminotetralines and particularly the compound (R,S)-2-amino-6-fluoro-7-methoxytetraline (ST 626).

The 6,7-substituted-2-aminotetralines for the use according to the present invention are also known compounds but for completely different therapeutic applications. In fact, in J Chem Soc (1997), 288–93 they are described as possessing bronchodilatory activity; in Tetrahedron let, 22/38, 3707–10, 1981 they are described as compounds endowed with dopaminergic activity.

It is clear that there is no relationship between the known bronchodilatory and dopaminergic activity of such aminotetralines and their therapeutic activity in septic shock and in inflammatory and/or autoimmune pathologies in which the aetiopathogenetic role of the inflammatory cytokines is well established.

The inflammatory and/or autoimmune pathologies to be treated with the compounds of the invention described herein are, for example, rheumatoid arthritis, pancreatitis, inflammatory bowel disease, systemic lupus erythematosus, glomerulo-nephritis and encephalomyelitis.

Hereinafter, reference will be made only to septic shock, it being understood that the other pathologies due to inflammatory cytokines can also be effectively treated according the invention.

Septic shock is an extremely severe clinical syndrome which may set in as a result of infections mainly caused either by gram-negative or gram-positive bacteria, by protozoa or by viruses, and characterised by leukocytosis, fever, tachycardia, hypotension and renal, respiratory, cardiac and hepatic insufficiency. It should be stressed, however, that the severity of septic shock is independent of the type of micro-organism responsible for the syndrome (Parrillo J. E., Pathogenetic mechanisms of septic shock, N Engl J Med, 328:1471–1477, 1993) but is related to the individual inflammatory response to the antigen responsible for the toxic insult. Despite the significant improvement in antibiotic therapy and in intervention protocols in intensive care units over the past few years, shock remains one of the major causes of morbidity and mortality in hospitalised patients. It is estimated that in the USA it is responsible for approximately 100,000 deaths/year (Glauser M. P., Zanetti G., Baumgartner J. D. and Cohen J., Septic shock: pathogenesis, Lancet, 338:732–736, 1991).

The most decisive and characteristic feature of septic shock is the body's reaction to products deriving from lysis or from microbial metabolism.

The first of these substances to be identified and the one most used in experimental research is lipopolysaccharide (LPS), a constituent of the gram-negative bacterial wall chemically consisting is in a polysaccharide portion which varies according to the bacterial species and a lipid portion (lipid A) which is constant, and present in the blood of septicaemic subjects in the form of micelles. If administered to animals, LPS is capable of reproducing all the cardiocirculatory and neurological symptoms encountered in shock (Olson C., Salzer W. L., McCall C. E., Biochemical, physiological and clinical aspects of endotoxaemia, Molec Aspects Med, 10: 511–629, 1988). It is therefore identifiable as the prime mover in the chain of events, which leads to the triggering of the clinical symptoms via activation of the intrinsic and extrinsic pathways of the coagulative cascade and the secretion of cytokines of mainly macrophage-monocyte origin, such as, for instance, TNF, IL-1 and IL-6.

The increasing importance this syndrome has come to take on over the past few years, its severity and the inadequate therapeutic measures currently available make the rapid discovery of therapeutic agents capable of effectively combating the progression of the disease a highly desirable goal.

It has now been found that a class of known 6,7-substituted 2-aminotetralines exhibits potent activity in the prevention and therapeutic treatment of the above-mentioned pathologies.

6,7-Substituted-2-aminotetralines according to the invention can occur both as free bases with general formula (I):

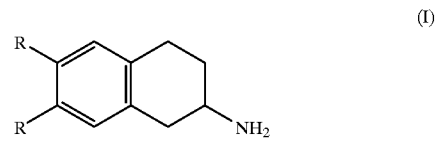

and as pharmacologically acceptable salts with general formula (II):

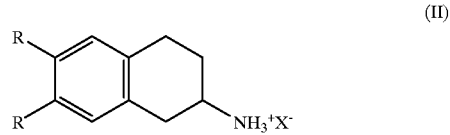

wherein:
R is methoxy or hydroxy and
X⁻ is the monovalent anion of a pharmacologically acceptable acid.

Among the 6,7-substituted-2-aminotetralines with general formula (I) or (II) the following compounds are particularly preferred wherein:
R=methoxy: (R,S)-2-amino-6,7-dimethoxytetraline hydrochloride (hereinafter: ST 1213)
R=OH: (R, S)-2-amino-6,7-dihydroxytetraline hydrochloride (hereinafter: ST 1236).

What is meant by pharmacologically acceptable salts of 6,7-substituted-2-aminotetralines with formula (I) are any of its salts with an acid that does not give rise to unwanted toxic or side effects. Such acids are well known to pharmacologists and to experts in pharmacy and pharmaceutical technology.

Non-limiting examples of such salts are chloride, bromide, orotate, acid aspartate, acid citrate, acid phosphate, fumarate and acid fumarate, lactate, maleate and acid maleate, acid oxalate, acid sulphate, glucose phosphate, tartrate and acid tartrate. FDA-approved salts are listed in Int J Pharm 33 (1986), 201–217, which is incorporated herein for reference purposes.

The methodological approach most widely employed for the purposes of assessing the possible protective effect of a substance in septic shock, in preclinical investigation, is the use of experimental models of intoxication with a toxic substance (exo- or endotoxin) injected directly into the laboratory animal or released in massive amounts by the infecting cells with which the animal is inoculated.

Here below are given the results obtained with the according to the invention, (R,S)-2-amino-6,7-dimethoxytetraline hydrochloride (ST 1213) and (R,S)-2-amino-6,7-dihydroxytetraline hydrochloride (ST 1236), in comparison with the reference compound (R,S)-2-amino-6-fluoro-7-methoxytetraline hydrochloride (ST 626). As mentioned above, the compound ST 626 is the compound known to be most closely related structurally to the compounds for use as per the invention and also known to be endowed with the same pharmacological activity.

These results demonstrate the preventive and therapeutic activity of the compounds according to the invention (ST 1213 and ST 1236) in comparison with the known compound ST 626 and also provide indications as to one of the possible mechanisms of action responsible for the favourable pharmacological profile of the compounds: a drastic reduction in blood levels of inflammatory cytokines (TNF, IL-1beta, IL-6, IFN-γ levels, and in serum nitric oxide (NOx) levels.

Evaluation of the Effects of ST 1213 and ST 1236 in Animal Models of Septic Shock.

Male BALB/C mice (C. River) aged approx. 6 weeks were utilised (10 animals per experimental group). The animals, housed in cages at a constant temperature 22±2° C. and 50±15% relative humidity with 12 hours of light (7am–7pm) and 12 hours of darkness (7 pm–7 am), had unrestricted access to food and drinking water.

The compounds tested were ST1213, ST 1236 and ST 626 (reference compound). The pH of the compound solutions was corrected, as necessary, with NaOH 0.1 N (maintaining the solution cold and under stirring) to obtain values no lower than pH 5.5.

The substances utilised were: LPS (Escherichia coli serotype O26:B6), batch 73570 JB (Difco), LPS (Salmonella typhosa), batch 81H4018 (Sigma), SEB (Staphylococcus aureus), batch 144H4024 (Sigma), and D-galactosamine batch 031EE002485 (Merck).

Lethality Induced by E. coli and S. typhosa LPS

Animals were treated with LPS from E. coli or S. typhosa. Prior to use the endotoxin was first dissolved in sterile saline and then injected intraperitoneally (i.p.) in a volume of 200 μL at doses of 10.0–12.5 mg/kg (E. coli) and 23.0–27.0 mg/kg (S. typhosa), corresponding to approximately the LD80.

The compounds tested were administered intravenously (i.v.) in a volume of 200 μL of sterile saline, corresponding to approximately 1/10 of the respective LD50s, 30 min before and again min after treatment with LPS, or 5 and 30 min after the endotoxic challenge.

Lethality Induced by E. coli LPS in Mice Sensitised with D-galactosamine

Animals were sensitised with D-galactosamine (1000 mg/kg i.p.) and, at the same time, treated with E. coli LPS (0.30 mg/kg i.p.) in a total volume of 200 μL. The dose of LPS utilised corresponded approximately to the endotoxin $LD_{80}$ in the animals sensitised with D-galactosamine.

The compounds tested were administered intravenously (i.v.) in a volume of 200 μL of sterile saline at the dose corresponding approximately to 1/10 of the respective $LD_{50}$s, 30 min before and 5 min after, or 5 and 30 min after the LPS challenge.

Lethality Induced by SEB (Staphylococcus aureus) in Mice Sensitised with D-galactosamine Animals were sensitised with D-galactosamine (1000–1500 mg/kg i.p.) and, at the same time, treated with the enterotoxin SEB (3 mg/kg i.p.) in a total volume of 200 μL. The dose of SEB utilised corresponds to approximately the $LD_{80}$ and was determined in a preliminary experiment.

The compounds tested were administered intravenously (i.v.) in a volume of 200 μL of sterile saline at the dose corresponding approximately to 1/10 of the respective $LD_{50}$s, 30 min before and 5 min. after, or 5 min. and 30 min. after the SEB challenge.

The animals were observed for 10 days in all experiments, taking daily note of any deaths.

The statistical significance of the protective effect of the study compounds was evaluated using t he one-tailed Fishers exact test.

Results

Lethality Induced by E. coli LPS

The results obtained with this experimental model of shock with E. coli LPS are reported in Table 1 (A and B). The compound ST1213 significantly reduces the lethality induced by LPS (p<0.001), when it is administered 30 min before and 5 min after the LPS challenge (Tab. 1A). Such protection is also obtained in the post-challenge treatment protocol, though the degree of statistical significance is lower (p<0.05) (Tab. 1B).

TABLE 1

Protective effect of ST 1213 i.v. administration on lethality induced in mice by injection of E. coli LPS. Pre- and post-challenge treatment (−30 and +5 min) (A) or post-challenge only (+5 and +30 min) (B).

| Treatment (dose) | Deaths/total | Increase[a] in survival (%) | P[b] |
|---|---|---|---|
| A | | | |
| LPS control | 31/39 | — | — |
| ST 626 (6 mg/kg, i.v.) | 25/38 | +14 | n.s. |
| LPS control | 25/38 | — | — |
| ST 1213 (6 mg/kg, i.v.) | 10/30 | +47 | <0.001 |
| B | | | |
| LPS control | 20/21 | — | — |
| ST 1213 (6 mg/kg, i.v.) | 14/20 | +15 | <0.05 |

[a]= increase in survival (%) of treated animals compared to LPS control.
[b]= Statistical significance calculated using one-tailed Fisher's exact test.

Lethality Induced by S. typhosa LPS

In this experimental model of endotoxic shock with S. typhosa LPS, the compounds ST 1213 and ST 1236 significantly reduce lethality when administered pre- and post-challenge, p<0.001 and p<0.05, respectively (Tab. 2).

ST 1213, when administered in a second post-challenge treatment protocol, retains its protective efficacy, though to a lesser extent (Tab. 3).

TABLE 2

Protective effect of ST 1213 and ST 1236 i.v.
administration on lethality induced in mice by injection of
S. typhosa LPS. Pre- and post-challenge treatment (−30
and +5 min).

| Treatment (dose) | Deaths/total | Increase[a] in survival (%) | P[b] |
|---|---|---|---|
| LPS control | 14/20 | — | — |
| ST 626 (6 mg/kg, i.v.) | 6/20 | +40 | <0.05 |
| LPS control | 14/20 | — | — |
| ST 1213 (6 mg/kg, i.v.) | 2/20 | +60 | <0.001 |
| LPS control | 16/20 | — | — |
| ST 1236 (19 mg/kg, i.v.) | 9/20 | +35 | <0.05 |

[a] = increase in survival (%) of treated animals compared to LPS control.
[b] = Statistical significance calculated using one-tailed Fisher's exact test.

TABLE 3

Protective effect of ST 1213 i.v. administration on lethality
induced in mice by injection of S. typhosa LPS. Post-
challenge treatment (+5 and +30 min).

| Treatment (dose) | Deaths/total | Increase[a] in survival (%) | P[b] |
|---|---|---|---|
| LPS control | 22/30 | — | — |
| ST 1213 (6 mg/kg, i.v.) | 14/30 | +27 | <0.05 |

[a] = increase in survival (%) of treated animals compared to LPS control.
[b] = Statistical significance calculated using one-tailed Fisher's exact test.

Lethality Induced by E. coli LPS in Mice Sensitised with D-galactosamine

Animals were sensitised with D-galactosamine and at the same time treated with E. coli LPS. The compound ST 1236 significantly reduces the lethality (p<0.001) (Tab. 4).

TABLE 4

Protective effect of ST 1236 i.v. administration on lethality
induced by injection of E. coli LPS in mice sensitised with
D-galactosamine. Pre- and post-challenge treatment (−30 and +5 min).

| Treatment (dose) | Deaths/total | Increase[a] in survival (%) | P[b] |
|---|---|---|---|
| LPS + D-GalN control | 25/29 | — | — |
| ST 626 (6 mg/kg, i.v.) | 21/28 | +11 | n.s. |
| LPS + D-GalN control | 17/20 | — | — |
| ST 1236 (19 mg/kg, i.v.) | 4/19 | +64 | <0.001 |

[a] = Increase in survival (%) of treated animals compared to LPS + D-GalN control.
[b] = Statistical significance calculated using one-tailed Fisher's exact test.

Lethality Induced by Enterotoxin SEB (*Staphylococcus aureus*) in Mice Sensitised with D-galactosamine The results obtained with this experimental model of shock with enterotoxin SEB in mice sensitised with D-galactosamine are reported in Tables 5 and 6.

The compounds ST 1213 and ST 1236 reduce the lethality in comparison with the control (increases in survival=46% and 90%, respectively) when administered 30 min before and 5 min after the challenge (Tab. 5). Following the post-challenge treatment the protective effect remains, but fails to prove statistically significant (Tab. 6).

TABLE 5

Protective effect of ST 1213 and ST 1236 i.v. administration on
lethality induced by injection of LPS from enterotoxin SEB in mice
sensitised with D-galactosamine. Pre- and post-challenge
treatment (−30 and +5 min).

| Treatment (dose) | Deaths/total | Increase[a] in survival (%) | P[b] |
|---|---|---|---|
| SEB + D-GalN control | 19/28 | — | — |
| ST 1213 (6 mg/kg i.v.) | 6/28 | +46 | <0.001 |
| SEB + D-GalN control | 18/20 | — | — |
| ST 1236 (19 mg/kg i.v) | 0/20 | +90 | <0.001 |

[a] = Increase in survival (%) of treated animals compared to LPS control.
[b] = Statistical significance calculated using one-tailed Fisher's exact test.

TABLE 6

Protective effect of ST 1213 and ST 1236 i.v. administration on lethality
induced by injection of LPS from enterotoxin SEB in mice sensitised with
D-galactosamine. Post-challenge treatment (−30 and +5 min).

| Treatment (dose) | Deaths/total | Increase[a] in survival (%) | P[b] |
|---|---|---|---|
| SEB + D-GalN control | 18/20 | — | — |
| ST 1213 (6 mg/kg, i.v.) | 14/20 | +20 | n.s. |
| SEB + D-GalN control | 16/20 | — | — |
| ST 1236 (19 mg/kg, i.v.) | 10/20 | +30 | n.s. |

[a] = Increase in survival (%) of treated animals compared to LPS control.
[b] = Statistical significance calculated using one-tailed Fisher's exact test.

Evaluation of the Effect of ST 1213 and ST 1236 on Serum TNF (Tumor Necrosis Factor) Levels Induced by LPS in Rat Whole Blood Culture Cultures of whole blood cells stimulated by LPS have been utilised in recent years as an experimental model, which, though presenting a number of limitations, mimics the physiopathological condition of endotoxaemia, a situation in which the lipopolysaccharide of gram-negative bacteria is released into the blood stream, thus coming into contact with the immune system cells. This experimental model, in fact, has recently been adopted for the evaluation of potential inhibitors of the release of TNF and IL-1 (G C Rice et al., Shock, 4:254–266, 1994. A J H Gearing et al., Nature, 370:555–557, 1994. K Tschaikowsky, Biochim Biophys Acta, 1222:113–121, 1994. A Haziot et al., J Immunol, 152:5868–5876, 1994).

Male Wistar rats (C. River) weighing 175–200 g were utilised in these experiments.

The animals, housed in cages at a constant temperature of 22±2° C. and 50±15% relative humidity with 12 hours of light (7 am–7 pm), had unrestricted access to food and drinking water.

The compounds tested were ST 1213 and ST 1236.

The endotoxin utilised was LPS from *Salmonella typhosa*, batch 81H4018 (Sigma).

Heparinised blood samples (0.450 mL/test tube) were taken from Wistar rats sacrificed by decapitation. Volumes of 0.025 mL (20× solution) of the compounds tested (final concentration 0.050 mM) dissolved in sterile saline were added to the test tubes containing the blood samples. 0.025 mL (20× solution) of LPS from *Salmonella typhosa* were added (final LPS concentration=1 μg/mL) to the test tubes incubated for 1 h at 37° C. in a 5% CO2 humidified atmosphere. The test tubes were incubated in the same conditions for 4 h and then centrifuged for 5 min at 10,000 rpm and the supernatants were stored frozen at −80° C. pending TNF assay.

TNF biological activity was determined in RPMI medium added with 1% FCS. For the TNF assay serial dilutions of the samples (50 μL) containing TNF (TNF standard, culture supernatants, serum, biological fluids, etc.) were made directly in the 96-well Primaria microtitre plates. Actinomycin D-mannitol (50 μL) at a final concentration of 4 μg/mL, prepared in RPMI medium added with 1% FCS, was added to the wells. This inhibitor enhances cell sensitivity to TNF.

100 μL of a standardised suspension of $4 \times 10^5$ cells/mL of L929 (murine fibrosarcoma sensitive to the toxic action of TNF) was is added to each well. Appropriate controls, i.e. the Actinomycin D control (cells+Actinomycin but without TNF) and the cell control (cells in the presence of culture medium alone), were also prepared.

After further incubation for 18 h at 37° C. with 5% CO2, the cells were stained with a freshly prepared solution of 1 mg/mL XTT (sodium 3'-[1-[(phenylamino)-carbonyl]-3,4-tetrazolium]-bis(4-methoxy-6-nitro)benzene-sulphonic acid hydrate) and 125 μM PMS (phenazine methosulphate) according to the method described here below.

The PMS mother solution is 100 mM (stable for about 20 days at +4° C. in the dark) and is prepared by dissolving PMS in PBS, followed by brief sonication to dissolve the PMS completely. The 100 mM PMS solution is then diluted 1:800 in XTT, thus obtaining a final PMS concentration of 125 μM in XTT 1 mg/ml. The XTT-PMS staining mixture must be filtered prior to use.

On completing the 18 h incubation, cells were stained by adding 50 μL of the XTT-PMS staining solution to each well, thus obtaining a final volume of 250 μL with final XTT and PMS concentrations of 0.2 mg/mL and 25 μM, respectively. A "blank", consisting of wells containing 200 μL of culture medium +50 μL of XTT-PMS staining solution, was also prepared.

The microtitre plates were incubated for 2–2.5 hours at 37° C. with 5% CO2 (total incubation time=about 20 hours).

The absorbance values of each sample were measured with a microtitre plate reader using a 450 nm readout wavelength and a 620 nm reference wavelength (the calorimetric microtiter plate reader was programmed to automatically deduct the "blank" absorbance value from the sample value).

The TNF titre was calculated as described here below. By definition, 1 unit of biological activity is given by the semimaximal value (=50%) of the Actinomycin-D absorbance.

Sample dilutions give rise to an absorbance value curve whose linear portion is described by the equation y=ax+b. After inserting the a and b values (obtained by computerised linear regression analysis) and after substituting for y the semimaximal absorbance value (corresponding to 1 biological unit) of the Actinomycin-D control, the equation is resolved for x, which represents the reciprocal of the sample dilutions. The value obtained gives the TNF titre expressed in U/mL.

Data were analysed using the two-tailed Student's t-test.

Results

The results obtained with this experimental model and reported in Table 7 show that the compounds tested reduce, though to different extents, TNF production by the blood culture stimulated with LPS. In fact, the compounds ST 1236 and ST 1213 induce 59% and 31% reductions, respectively, in TNF levels.

TABLE 7

Effect of compounds ST 1213 and ST 1236 on TNF production induced in rat blood cultures (n° = 5) stimulated with S. typhosa LPS (1 μg/mL). The compounds were tested at a concentration of 50 μM. The experimental conditions were those described in Materials and Methods.

| Treatment | TNF (mean % value) | Stand. Dev. | P* |
|---|---|---|---|
| LPS | 100 | 0 | — |
| LPS + ST 1213 | 69 | 22 | <0.02 |
| LPS + ST 1236 | 41 | 15 | <0.001 |

*Statistical significance evaluated using two-tailed Student's t test.

Evaluation of the Effect of ST 1213 and ST 1236 on Serum TNF Levels Induced by LPS in Mice Male BALB/c mice (C. River), aged approx. 6 weeks were utilised (10 animals per experimental group).

The animals, housed in cages at a constant temperature of 22±2° C. and 50±15% relative humidity with 12 hours of light (7 am–7 pm) and 12 hours of darkness (7 pm–7 am), had unrestricted access to food and drinking water.

The compounds tested were ST1213, ST 1236 and ST 626 (reference compound). The pH of the compound solutions was corrected, as necessary, with NaOH 0.1 N (maintaining the solution cold and under stirring) to obtain values no lower than pH 5.5.

The substances utilised were: LPS (from E. coli serotype O26:B6, batch 73570 JB (Difco), LPS (Salmonella typhosa), batch 81H4018 (Sigma), D-galactosamine, batch 031EE002485 (Merck).

Lethality Induced by E. coli and S. typhosa LPS

The experimental conditions were exactly the same as those previously described.

Lethality Induced by E. coli LPS in Mice Sensitised with D-galactosamine

The experimental conditions were exactly the same as those previously described.

In both the experimental models the blood samples were taken 90 min after the challenge (TNF serum peak level).

Ether-anaesthetised mice were bled by retro-orbital sinus puncture. Blood samples were incubated at room temperature for 2 h and the serum thus obtained was centrifuged for 20 min at 3000 rpm and stored frozen at −80° C. pending TNF assay.

TNF biological activity was determined in RPMI medium containing 1% FCS.

50 μL/well serial dilutions of the sample containing TNF were added directly to the Primaria microtitre plate. The experimental conditions utilised were the same as those previously described.

Data were analysed using the one-tailed Student's t-test.

Results

Lethality Induced by E. coli and S. typhosa LPS

The results obtained in these experimental models show that the compound ST 1213 significantly reduces TNF levels induced by E. coli LPS (p<0.01) (Tab. 8) and produces an even more substantial reduction in serum TNF levels in the experiment with Salmonella typhosa LPS (p<0.0001) (Tab. 9).

TABLE 8

Effect of ST 1213 administration (6 mg/kg i.v.) on serum TNF levels in
E. coli LPS septic shock model in mice. Pre- and post-challenge treatment
(−30 and +5 min).

| Treatment | TNF (U/mL) | | |
|---|---|---|---|
| | Mean | S. E. | P |
| LPS control | 50.0 | 12.4 | — |
| ST 1213 | 12.0 | 1.6 | 0.01 |

TABLE 9

Effect of ST 1213 administration (6 mg/kg i.v.) on serum TNF levels in
S. typhosa LPS septic shock model in mice. Pre- and post-challenge
treatment (−30 and +5 min).

| Treatment | TNF (U/mL) | | |
|---|---|---|---|
| | Mean | S. E. | P |
| LPS control | 154.2 | 41.0 | — |
| ST 626 | 35.0 | 10.0 | 0.01 |
| LPS control | 58.1 | 10.1 | |
| ST 1213 | 5.0 | 1.7 | 0.0001 |

Lethality Induced by E. coli LPS in Mice Sensitised with D-galactosamine

The results obtained with this experimental model of TNF production induced by E. coli LPS in animals sensitised with D-galactosamine are reported in Table 10.

The compound ST 1236 significantly reduces the release of TNF (p<0.000 1) induced by LPS in mice sensitised with D-galactosamine.

TABLE 10

Effect of ST 1236 administration (19 mg/kg i.v.) on serum TNF levels
induced by E. coli LPS in mice sensitised with D-galactosamine. Pre- and
post-challenge treatment (−30 and +5 min).

| Treatment | TNF (U/mL) | | |
|---|---|---|---|
| | Mean | S. E. | P |
| LPS + D.GalN control | 81.6 | 15.1 | — |
| ST 1236 | 0.4 | 0.1 | 0.0001 |

Evaluation of the Effect of ST 1213 ON Serum Interleukin-1 Beta (IL-1β), Interleukin-6 (IL-6) and Interferon-Gamma (IFN-γ) Levels Induced by E. coli or SEB Enterotoxin in Mice Male BALB/c mice (C. River), aged approximately 6 weeks, were utilised (10 animals per experimental group). The animals. housed in cages at a constant temperature of 22±2° C. and 50±15 relative humidity, with 12 hours of light (7 am–7 pm) and 12 hours of darkness (7 pm–7 am) had unrestricted access to food and drinking water.

The compound tested was ST 1213.

The substances utilised were: LPS from E. coli O26:B6, batch 73570 JB (Difco), SEB (Staphylococcus aureus), batch 144H4024 (Sigma), and D-galactosamine, batch 031EE002485 (Merck).

Lethality Induced by E. coli LPS

The experimental conditions were exactly the same as those previously described.

Lethality Induced by SEB from S. aureus in Mice Sensitised with D-galactosamine

The experimental conditions were exactly the same as those previously described.

In both models, blood samples were taken 2 h post-challenge for IL-6, 4 h post-challenge for IL-1β, and 6 h post-challenge for IFN-γ.

Ether-anaesthetised mice were bled by retro-orbital sinus puncture. Blood samples were incubated at room temperature for 2 h and the serum thus obtained was centrifuged for 20 min at 3000 rpm and stored frozen at −80° C. until assayed.

Biological assays were carried out according to the procedures indicated in the assay kits utilised. In particular, the following were used:

Mouse IL-1β Immunoassay (MLB00, R&D Systems)
Mouse IL-6 EIA Kit (8-6706, PerSeptive Diagnostics)
Mouse IFN-γ EIA Kit (8-6716, PerSeptive Diagnostics).

Data were analysed using the one-tailed Student's t-test.

Results

Lethality Induced by E. coli LPS

The results obtained with this experimental model are reported in Table 11.

The compound ST 1213 significantly reduces (p<0.0001) the production of IFN-gamma, but does not reduce the levels of the other two cytokines analysed .

TABLE 11

Effect of ST 1213 administration (6 mg/kg i.v.) on serum levels of
IL-1β, IL-6 and IFN-γ in mice stimulated with E. coli LPS.
Pre- and post-challenge treatment (−30 and +5 min).

| Treatment | −30 and +5 min protocol | | |
|---|---|---|---|
| | Mean | S. E. | P |
| | IL-1β(pg/mL) | | |
| LPS control | 162 | 28 | — |
| ST 1213 | 157 | 15 | n.s. |
| | IL-6 (pg/mL) | | |
| LPS control | 45995 | 8686 | — |
| ST 1213 | 56708 | 11304 | n.s. |
| | IFN-γ (pg/mL) | | |
| LPS control | 32 | 2 | — |
| | 9 | 1 | 0.0001 |

Lethality Induced by S. aureus SEB in Mice Sensitised with D-galactosamine

The results obtained with this experimental model are reported in Table 12.

The compound ST 1213 significantly reduces serum IL-1β and IL-6 levels but not serum IFN-γ levels.

TABLE 12

Effect of ST 1213 administration (6 mg/kg i.v.) on serum levels of
IL-1β, IL-6 and IFN-γ in mice stimulated with S. aureus SEB.
Pre- and post-challenge treatment (−30 and +5 min).

| Treatment | Mean | S. E. | P |
|---|---|---|---|
| | IL-1β(pg/mL) | | |
| SEB-D-GalN control | 18 | 4 | |
| ST 1213 | 1.6 | 0.6 | 0.001 |

TABLE 12-continued

Effect of ST 1213 administration (6 mg/kg i.v.) on serum levels of
IL-1β, IL-6 and IFN-γ in mice stimulated with *S. aureus* SEB.
Pre- and post-challenge treatment (−30 and +5 min).

| Treatment | Mean | S. E. | P |
|---|---|---|---|
| | IL-6 (pg/mL) | | |
| SEB-G-GalN control | 562 | 47 | — |
| ST 1213 | 182 | 69 | 0.001 |
| | IFN-γ (pg/mL) | | |
| SEB-D-GalN control | 40 | 3 | — |
| ST 1213 | 37 | 5 | n.s. |

Evaluation of the Effect of ST 1213 ON Serum Nitric Oxide (NOx) Induced by *E. coli* LPS in Mice Male BALB/c mice (C. River), aged approx. 6–7 weeks, were utilised (6–9 animals per experimental group).

The animals, housed in cages at a constant temperature of 22±2° C. and 50±15% relative humidity with 12 hours of light (7 am–7 pm) and 12 hours of darkness (7 pm–7 am), had unrestricted access to food and drinking water.

The compound tested was ST 1213.

The endotoxin utilised was LPS from *E. coli* 026:B6, batch 73570, Difco, previously dissolved in sterile saline, which was injected intraperitoneally at the dose of 5 mg/kg.

Compounds ST 1213 and ST 626 (reference compound) were administered i.v. at the dose of 6 mg/kg, corresponding to approximately 1/10 of the $LD_{50}$, +5 min and +30 min after the LPS challenge.

Ether-anaesthetised mice were bled by retro-orbital sinus puncture, taking blood samples 20 h after the LPS challenge, when NOx reached its serum peak levels in mice.

The blood, put into heparinised test tubes, was centrifuged for 10 min at 2200 rpm and stored frozen at −80 C pending NOx assay.

Before testing the samples were diluted 1:3 with distilled water and then centrifuged for 90 min at 4700 g on Ultrafree-MC, 10,000 NMWL Millipore filters (Cat. No. UFC3LGC00).

The sample assay for NOx was carried out using the recently marketed assay kit manufactured by Cabru (Nitrate/Nitrite assay kit, Cat. No. 780001).

Data were analysed using the two-tailed Student's t-test.

Results

The results obtained with this experimental model are reported in Table 13.

The compound ST 1213 significantly reduces NOx levels (42% reduction) induced by *E. coli* LPS in BALB/c mice, when administered post-challenge.

In the same experimental model, the reference compound ST 626 does not significantly reduce serum levels of NOx (21% reduction).

TABLE 13

Effect of ST 1213 administration (6 mg/kg i.v.). Treatment
5 and 30 min after the i.p. LPS challenge (5 mg/kg).

| Experimental condition | N. of samples | NOx (mM) Mean ± S. E. | Decrease in NOx[a] (%) | P[b] |
|---|---|---|---|---|
| LPS control | 6 | 453.54 ± 13.2 | — | — |
| ST 626 | 8 | 359.3 ± 37.9 | 21 | n.s. |
| LPS control | 9 | 891.0 ± 51.4 | — | — |
| ST 1213 | 9 | 518.0 ± 64.0 | 42 | <0.001 |

[a]= Decrease (%) in NOx levels of treated animals compared to the control group.
[b]= Statistical significance evaluated using the two-tailed Student's t-test.

What is claimed is:

1. A method of treating autoimmune conditions induced by inflammatory cytokines comprising administering to a patient in need of same an effective amount of a 6,7-substituted 2-aminotetraline of the general formula (I)

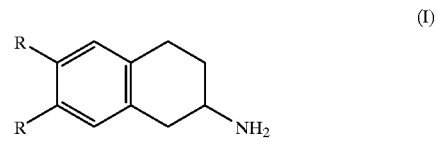

(I)

or a pharmacologically acceptable salt of the general formula (II)

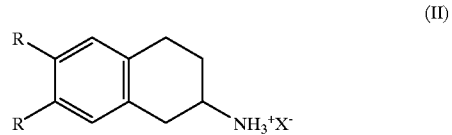

(II)

wherein:

R is methoxy or hydroxy, provided at least one R is hydroxy and

X⁻ is the monovalent anion of a pharmacologically acceptable acid.

2. The method according to claim 1, in which the condition treated is rheumatoid arthritis, pancreatitis, inflammatory bowel disease, systematic lupus erythematosus, glomerulonephritis or encephalomyelitis.

3. The method according to claim 1, in which the monovalent anion of the pharmacologically acceptable acid is selected from chloride, bromide, orotate, acid aspartate, acid citrate, acid phosphate, fumarate and acid fumarate, lactate, maleate and acid maleate, acid oxalate, acid sulphate, glucose phosphate, tartrate and acid tartrate.

4. The method according to claim 1, in which the 6,7-substituted 2-aminotetraline is (R,S)-2-amino-6,7-dimethoxytetraline hydrochloride.

5. The method according to claim 1, in which the 6,7-substituted 2-aminotetraline is (R,S)-2-amino-6,7-dihydroxytetraline hydrochloride.

6. A method of treating inflammatory conditions induced by inflammatory cytokines comprising administering to a patient in need of same an effective amount of a 6,7-substituted 2-aminotetraline of the general formula (I)

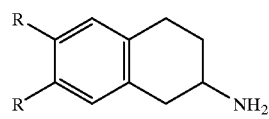

or a pharmacologically acceptable salt of the general formula (II)

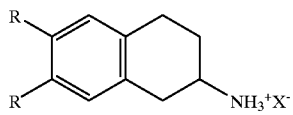

wherein:

R is methoxy or hydroxy, provided at least one R is hydroxy, and

X⁻ is the monovalent anion of a pharmacologically acceptable acid.

7. The method according to claim 6, in which the condition treated is rheumatoid arthritis, pancreatitis, inflammatory bowel disease, systematic lupus erythematosus, glomerulonephritis or encephalomyelitis.

8. The method according to claim 6, in which the monovalent anion of the pharmacologically acceptable acid is selected from chloride, bromide, orotate, acid aspartate, acid citrate, acid phosphate, fumarate and acid fumarate, lactate, maleate and acid maleate, acid oxalate, acid sulphate, glucose phosphate, tartrate and acid tartrate.

9. The method according to claim 6, in which the 6,7-substituted 2-aminotetraline is (R,S)-2-amino-6,7-dihydroxytetraline hydrochloride.

10. A method of preventing or treating septic shock comprising administering to a person in need of same an effective amount of a 6,7-substituted 2-aminotetraline of the general formula (I)

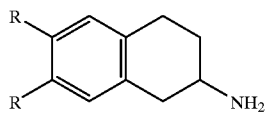

or a pharmacologically acceptable salt of the general formula (II)

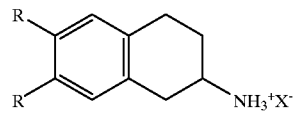

wherein:

R is methoxy or hydroxy, provided at least one R is hydroxy, and

X⁻ is the monovalent anion of a pharmacologically acceptable acid.

11. The method according to claim 10, in which the monovalent anion of the pharmacologically acceptable acid is selected from chloride, bromide, orotate, acid aspartate, acid citrate, acid phosphate, fumarate and acid fumarate, lactate, maleate and acid maleate, acid oxalate, acid sulphate, glucose phosphate, tartrate and acid tartrate.

12. The method according to claim 10, in which the 6,7-substituted 2-aminotetraline is (R,S)-2-amino-6,7-dihydroxytetraline hydrochloride.

* * * * *